(12) United States Patent
Ikeda et al.

(10) Patent No.: US 12,669,491 B2
(45) Date of Patent: Jun. 30, 2026

(54) INTERNAL OXIDATION STARTING TEMPERATURE ESTIMATION DEVICE, INTERNAL OXIDE LAYER THICKNESS ESTIMATION DEVICE, INTERNAL OXIDATION STARTING TEMPERATURE ESTIMATION METHOD, AND PROGRAM

(71) Applicant: NIPPON STEEL CORPORATION, Tokyo (JP)

(72) Inventors: Keita Ikeda, Tokyo (JP); Tooru Akashi, Tokyo (JP); Yasumitsu Kondo, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 509 days.

(21) Appl. No.: 18/034,628

(22) PCT Filed: Nov. 2, 2021

(86) PCT No.: PCT/JP2021/040383
§ 371 (c)(1),
(2) Date: Apr. 28, 2023

(87) PCT Pub. No.: WO2022/097636
PCT Pub. Date: May 12, 2022

(65) Prior Publication Data
US 2023/0296579 A1 Sep. 21, 2023

(30) Foreign Application Priority Data
Nov. 6, 2020 (JP) ................................. 2020-185640

(51) Int. Cl.
*G01N 33/2028* (2019.01)
*B21B 3/02* (2006.01)
(Continued)

(52) U.S. Cl.
CPC ........... *G01N 33/2028* (2019.01); *B21B 3/02* (2013.01); *C22C 38/02* (2013.01); *C22C 38/04* (2013.01); *C22C 38/06* (2013.01)

(58) Field of Classification Search
CPC .... B21B 3/02; B21B 3/00; B21B 1/26; C21D 9/46
See application file for complete search history.

(56) References Cited

U.S. PATENT DOCUMENTS 11,066,720 B2 * 7/2021 Fujii ........................ C21D 9/46

FOREIGN PATENT DOCUMENTS

JP     9-256066 A     9/1997
JP     2005-281793 A  10/2005
JP     2013-103235 A  5/2013

OTHER PUBLICATIONS

Kobayashi et al., "Improvement of Formability in Cold Rolling of Hot Band for Over 980 MPa Grade High Tensile Strength Steel Sheet", Tetsu-to-Hagane, vol. 100 (2014), No. 5, pp. 616-624.

* cited by examiner

*Primary Examiner* — Lam S Nguyen
(74) *Attorney, Agent, or Firm* — Birch, Stewart, Kolasch & Birch, LLP

(57) ABSTRACT
An internal oxidation starting temperature, estimation device estimates an internal oxidation starting temperature which is a minimum temperature required for an internal oxide layer to grow on a surface of an easily oxidizable element-containing hot-rolled steel sheet including Si, Mn, or Al or any combination thereof. The internal oxidation starting temperature estimation device includes an internal, oxidation starting temperature estimation unit that estimates the internal oxidation starting temperature on the basis of concentrations of the Si, the Mn, and the Al included in the easily oxidizable element-containing hot-rolled steel sheet.

6 Claims, 4 Drawing Sheets

(51) Int. Cl.
    *C22C 38/02*          (2006.01)
    *C22C 38/04*          (2006.01)
    *C22C 38/06*          (2006.01)

FIG. 8

INTERNAL OXIDATION STARTING TEMPERATURE ESTIMATION DEVICE, INTERNAL OXIDE LAYER THICKNESS ESTIMATION DEVICE, INTERNAL OXIDATION STARTING TEMPERATURE ESTIMATION METHOD, AND PROGRAM

TECHNICAL FIELD OF THE INVENTION

The present invention relates to an internal oxidation starting temperature estimation device, an internal oxide layer thickness estimation device, an internal oxidation starting temperature estimation method, and a program.

This application claims priority based on Japanese Patent Application No. 2020-185640 filed on Nov. 6, 2020, the content of which is incorporated herein by reference.

RELATED ART

In many cases, hot-rolled steel sheets manufactured by hot rolling cast pieces are coiled and then cooled. In this cooling step, an internal oxide layer is formed in a base metal portion immediately below a scale layer. The internal oxide layer is a layer in which metal oxides are dispersed at grain boundaries and in crystal grains. The metal oxide is mainly composed of an oxide of an element (for example, Si, Mn, Al, Cr, or the like) that is less noble than iron. The scale layer is relatively easily removed by a pickling step after the cooling process. However, it is difficult to remove the internal oxide layer, in the pickling step. Therefore, there is a problem that the excessive formation of the internal oxide layer significantly reduces the speed of the pickling step. In a steel material, such as high tensile strength steel (high-tensile steel), containing a large number of elements that are less noble than iron, the internal oxide layer is likely to be formed. Therefore, this problem is particularly remarkable, Therefore, a method for controlling an appropriate thickness of the internal oxide layer is required.

PRIOR ART DOCUMENT

Patent Document

[Patent Document 1] Japanese Unexamined Patent Application, First Publication No. 2013-103235
[Patent Document 2] Japanese Unexamined Patent Application, First Publication No. H9-256066
[Patent Document 3] Japanese Unexamined Patent Application, First Publication No. 2005-281793

Non-Patent Documents

[Non-Patent Document 1] Kobayashi et al., "Improvement of Formability in Cold Rolling of Hot Band for Over 980 MPa Grade High Tensile Strength Steel", Iron and Steel, Vol 100 (2014), No. 5, P 616-624

DISCLOSURE OF THE INVENTION

Problems to be Solved by the Invention

It is widely accepted that the thickness of the scale layer follows a so-called parabolic law. This is based on the assumption that the thickness of the scale layer is proportional to the square root of time. Meanwhile, findings for the thickness of the internal oxide layer have been described in Non-Patent Document 1 and Patent Document 1. However, it was not possible to accurately estimate the thickness of the internal oxide layer on the basis of these findings.

Specifically, Non-Patent Document 1 discloses that there is a temperature at which the generation of an internal oxide layer substantially starts (in other words, the minimum temperature required for the growth of the internal oxide layer, that is, an internal oxidation starting temperature Tcr), and that the internal oxide layer is not formed in a temperature range equal to or lower than the internal oxidation starting temperature. In addition, the thickness of the internal oxide layer is treated as being proportional to time. However, the thickness of the internal oxide layer is not simply proportional to time, which will be described in detail below.

Patent Document 1 discloses Expression Ain which the thickness of the internal oxide layer is proportional to the square root of a value obtained by integrating an Arrhenius growth rate over time. However, the presence of the internal oxidation starting temperature is not reflected in Expression A, and the integration is performed until the temperature falls below the internal oxidation starting temperature to reach room temperature, Therefore, there is also a problem in the accuracy of estimation.

$$\delta = \sqrt{\int_{t_c}^{t_e} a\exp\left(-\frac{b}{T}\right)dt} \ (m) \tag{A}$$

t; Time (second)
tc: Coiling start time (second)
te: Time until temperature reaches room temperature (second)
T: Absolute temperature (K)
a: 8 to $9\times10^{-6}$
b: 1.5 to $2.5\times10^{4}$ Patent Documents 2 and 3 disclose a technique for adjusting the coiling completion temperature of a hot-rolled steel sheet according to components of the hot-rolled steel sheet in consideration of the characteristics (adhesion and peeling resistance) of the scale layer. However, the technique disclosed in Patent Documents 2 and 3 does not control the thickness of the scale layer.

Meanwhile, according to the technique disclosed in Non-Patent Document 1, the internal oxide layer is formed in a temperature range higher than the internal oxidation starting temperature. Therefore, it is necessary to estimate the internal oxidation starting temperature with high accuracy in order to estimate the thickness of the internal oxide layer with high accuracy.

The invention has been made in view of the above problems, and an object of the invention is to provide an internal oxidation starting temperature estimation device, an internal oxide layer thickness estimation device, an internal oxidation starting temperature, estimation method, and a program that can estimate an internal oxidation starting temperature with higher accuracy.

Means for Solving the Problem

In order to solve the above problems according to an aspect of the invention, there is, provided an internal oxidation starting temperature estimation device that estimates an internal oxidation starting temperature which is a minimum temperature required for an internal oxide layer to grow on a surface of an easily oxidizable element-containing hot-rolled steel sheet including Si, Mn, or Al or any combination thereof. The internal oxidation starting temperature estimation device includes an internal oxidation starting temperature estimation unit that estimates the internal oxidation starting temperature on the basis of concentrations of the Si, the Mn, and the Al included in the easily oxidizable element-containing hot-rolled steel sheet.

Here, the internal, oxide layer may be formed when the easily oxidizable element-containing hot-rolled steel sheet is cooled in a coiled state.

In addition, the internal oxidation starting temperature estimation unit may set a temperature at which the internal oxide layer starts to be formed on the surface of the easily oxidizable element-containing hot-rolled steel sheet as the internal oxidation starting temperature on the basis of a measured value of a thickness of the internal oxide layer formed in the easily oxidizable element-containing hot-rolled steel sheet.

Further, the easily oxidizable element-containing hot-rolled steel sheet may be coiled, and the internal oxidation starting temperature estimation unit may generate a thickness-coiling temperature correlation graph showing a correspondence relationship between a coiling completion temperature, which is a temperature when the coiling of the easily oxidizable element-containing hot-rolled steel sheet is completed, and a measured value of a thickness of the internal oxide layer for each of a plurality of types of the easily oxidizable element-containing hot-rolled steel sheets in which the Si concentration, the Mn concentration, or the Al concentration or any combination thereof is different and may extrapolate the thickness-coiling temperature correlation graph to calculate, as the internal oxidation starting temperature, the coiling completion temperature when the thickness of the internal oxide layer is zero.

Furthermore, the internal oxidation starting temperature estimation unit may determine the internal oxidation starting temperature such that a correlation between a measured value of a thickness of the internal oxide layer and a cumulative temperature defined by the following Expression (1) is the highest, for each of a plurality of types of the easily oxidizable element-containing hot-rolled steel sheets in which the Si concentration, the Mn concentration, or the Al concentration or any combination thereof is different.

$$S_T = \int_{t0}^{t1} (T - Tcr)dt \qquad (1)$$

In Expression (1), $S_T$ is the cumulative temperature, T is a temperature of a portion to be estimated, in which the thickness of the internal oxide layer is to be estimated in the easily oxidizable element-containing hot-rolled steel sheet, Tcr is the internal oxidation starting temperature, t0 is an estimation start time when estimation of the thickness of the internal oxide layer is started, t1 is an estimation evaluation time, and T−Tcr is 0 in an integration interval where T−Tcr is equal to or less than 0.

Moreover, the internal oxidation starting temperature estimation unit may determine the internal oxidation starting temperature such that a sum of squared deviations when a quadratic function of the cumulative temperature is applied to the measured value of the thickness of the internal oxide layer is minimized, for each of the plurality of types of easily oxidizable element-containing hot-roiled steel sheets in which the Si concentration, the Mn concentration, or the Al concentration or any combination thereof is different.

According to another aspect of the invention, there is provided an internal oxide layer thickness estimation device including an internal oxide layer thickness estimation unit that estimates the thickness of the internal oxide layer formed in the easily oxidizable element-containing hot-rolled steel sheet, on the basis of the internal oxidation starting temperature estimated by the above-described internal oxidation starting temperature estimation device and the following Expression (2).

$$H = \alpha \times S_T + H_0 \qquad (2)$$

In Expression (2), H is the thickness of the internal oxide layer, $S_T$ is the cumulative temperature, $\alpha$ is a proportional constant, and $H_0$ is an initial value of the thickness of the internal oxide layer.

According to still another aspect of the invention, there is provided an internal oxidation starting temperature estimation method that estimates an internal oxidation starting temperature which is a minimum temperature required for an internal oxide layer to grow on a surface of an easily oxidizable element-containing hot-rolled steel sheet including Si, Mn, or Al or any combination thereof. The internal oxidation starting temperature estimation method includes an internal oxidation starting temperature estimation step of estimating the internal oxidation starting temperature on the basis of concentrations of the Si, the Mn, and the Al included in the easily oxidizable element-containing hot-rolled steel sheet.

According to yet another aspect of the invention, there is provided a program that causes a computer to estimate an internal oxidation starting temperature which is a minimum temperature required for an internal oxide layer to grow on a surface of an easily oxidizable element-containing hot-rolled steel sheet including Si, Mn, or Al or any combination thereof. The program causes the computer to execute an internal oxidation starting temperature estimation step of estimating the internal oxidation starting temperature on the basis of concentrations of the Si, the Mn, and the Al included in the easily oxidizable element-containing hot-rolled steel sheet.

Effects of the Invention

According to the above-described aspects of the invention, the internal oxidation starting temperature, which is the minimum temperature required for the internal oxide layer to grow on the surface of the easily oxidizable element-containing hot-rolled steel sheet including Si, Mn, or Al or any combination thereof, is estimated on the basis of the concentrations of the Si, the Mn, and the Al included in the easily oxidizable element-containing hot-rolled steel sheet. Therefore, it is possible to estimate the internal oxidation starting temperature with higher accuracy.

BRIEF DESCRIPTION OF THE DRAWINGS

FIG. 8 is a diagram showing a hardware configuration of an internal oxide layer thickness estimation device according to this embodiment.

EMBODIMENTS OF THE INVENTION

Figure 1:
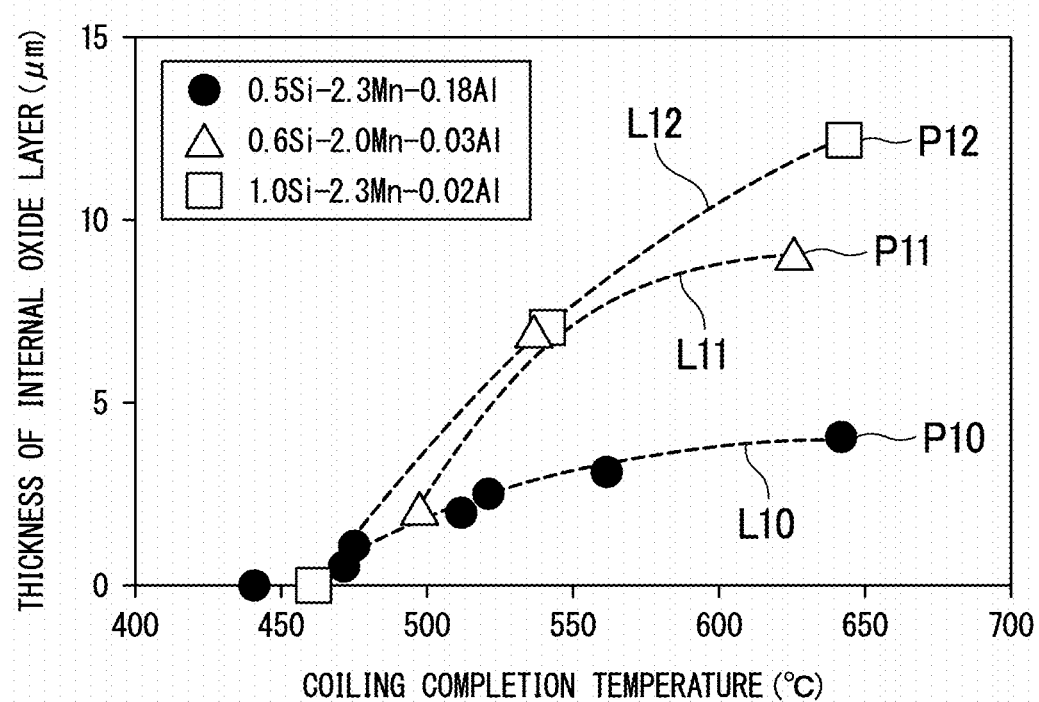
FIG. 1 is a thickness-coiling temperature correlation graph showing correspondence relationship between a coiling completion temperature of a hot-rolled steel sheet and a measured value of a thickness of an internal oxide layer for each composition of the hot-rolled steel sheet.

Hereinafter, preferred embodiments of the invention will be described in detail with reference to the accompanying drawings. The inventors thoroughly studied parameters having a high correlation with a thickness of an internal oxide layer in order to estimate an internal oxidation starting temperature and thus the thickness of the internal oxide layer. As a result, the inventors found that a cumulative temperature described below had a very high, correlation with the thickness of the internal oxide layer. Furthermore, it was found that the internal oxidation starting temperature affecting the cumulative temperature fluctuated depending on the composition of a hot-rolled steel sheet, particularly, Si, Mn, and Al concentrations. A processing device (a combination of an internal oxidation starting temperature estimation device and an internal oxide layer thickness estimation device) according to this embodiment is achieved on the basis of these findings.

<1. Type of Hot-Rolled Steel Sheet>

The hot-rolled steel sheet to be processed by the processing device according to this embodiment (the internal oxidation starting temperature and the thickness of the internal oxide layer are estimated by the processing device) is a hot-rolled steel sheet having an internal oxide layer formed therein. Specifically, the hot-rolled steel sheet is an easily oxidizable element-containing hot-rolled steel sheet including Si, Mn, or Al or any combination thereof, for example, 0.2 mass % or more of Si, 0.5 mass % or more of Mn, and 0.01 mass % or more of Al. Of course, the content of each element is not limited to this example. All of the elements are less noble than iron. That is, the "easily oxidizable element" in this embodiment means an element that is "more likely to be oxidized (more easily oxidizable) than Fe". The easily oxidizable element-containing hot-rolled steel sheet may further include elements, such as Cr, other than these elements. Examples of the easily oxidizable element-containing hot-rolled steel sheet include high tensile strength steel (high-tensile steel) and the like. In particular, the high-tensile steel is a preferable example of the object to which this embodiment is applied because the internal oxide layer is easily formed. Hereinafter, it is assumed that, unless otherwise specified, the "hot-rolled steel sheet" indicates the "easily oxidizable element-containing hot-rolled steel, sheet".

A thermal history of the hot-rolled steel sheet is not particularly limited. For example, the hot-rolled steel sheet is coiled and then cooled by any cooling method such as air cooling or water cooling (cooling step). In this cooling step, the internal oxide layer is formed immediately below a scale layer. In this case, the thermal history of the hot-rolled steel sheet follows a relatively simple cooling process. Of course, the thermal history of the hot-rolled steel sheet is not limited to this example. For example, the hot-rolled steel sheet may be cooled to a certain temperature in the cooling step after being coiled and then may be soaked or reheated for the purpose of annealing or the like. Further, the above-described cooling, annealing, and the like may be performed on the hot-rolled steel sheet in an uncoiled state in which the hot-rolled steel sheet is stretched into a flat sheet shape. Furthermore, the hot-rolled steel sheet may be cooled to a temperature that is equal to or lower than an internal oxidation starting temperature Tcr which will be described below and then may be reheated to a temperature that is equal to or higher than the internal oxidation starting temperature Tcr. That is, in the calculation of the cumulative temperature which will be described below, there may be an integration interval in which the temperature T of a portion to be estimated is equal to or lower than Tcr. In this integration interval, T−Tcr may be set to 0, which will be described below.

<2. Overall Configuration of Processing Device>

Figure 6:
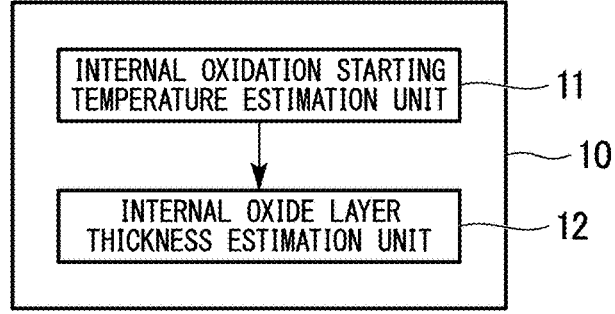
FIG. 6 is a functional block diagram showing a configuration of a processing device according to this embodiment.
Figure 8:
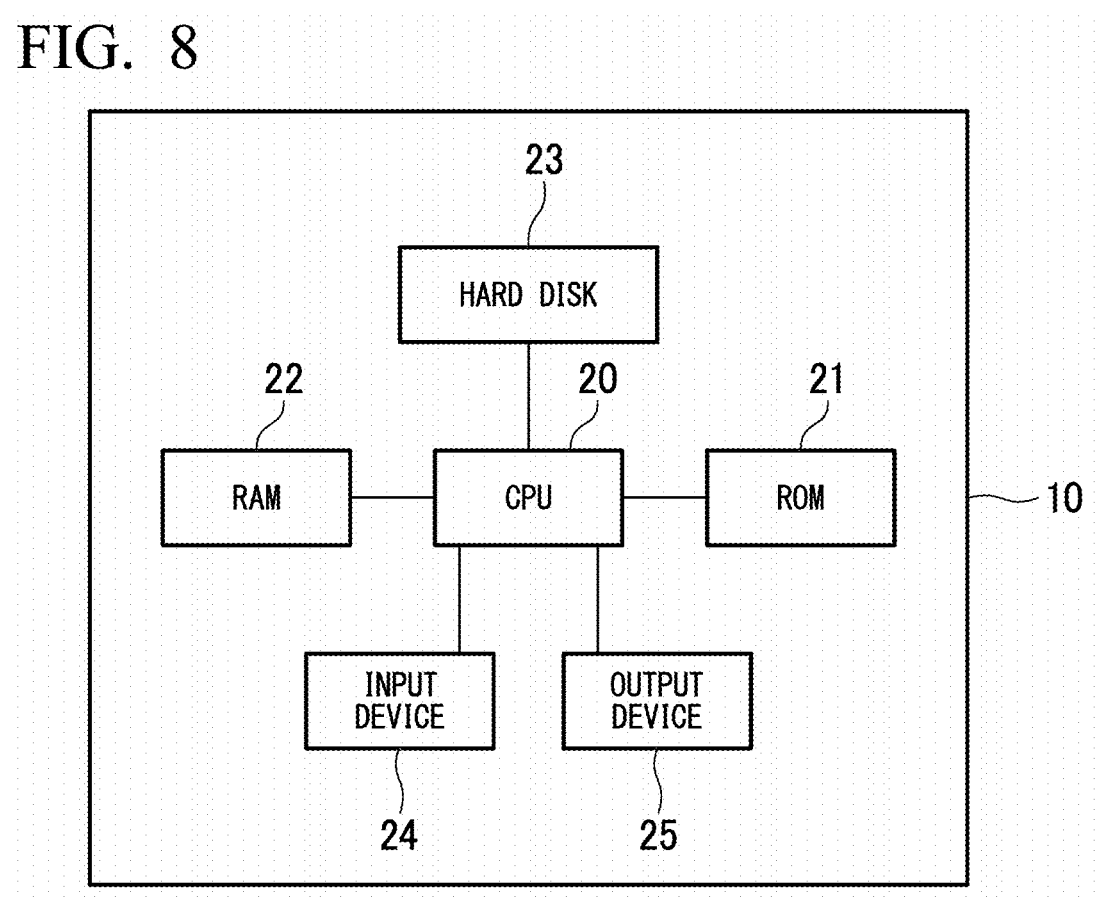

FIG. 6 is a functional block diagram showing an overall configuration of a processing device 10 according to this embodiment. The processing device 10 has the functions of both the internal oxidation starting temperature estimation device and the internal oxide layer thickness estimation device. That is, the processing device 10 has an internal oxidation starting temperature estimation unit 11 and an internal oxide layer thickness estimation unit 12. Of course, these components may be provided in separate device configurations. As shown in FIG. 8, the processing device 10 includes a CPU 20 a, ROM 21, a RAM 22, a hard disk 23, various input devices (for example, a keyboard and a mouse) 24 and various output devices (for example, a display) 25 as a hardware configuration. For example, a program that causes the processing device 10 to function as the internal oxidation starting temperature estimation unit 11 and the internal oxide layer thickness estimation unit 12 is recorded on the ROM. The CPU reads and executes the program. The RAM serves as a work area of the CPU. An operator can input various types of information to the processing device 10 using the input device. In addition, the processing device 10 outputs various types of information to the output device. Hereinafter, for example, processes performed by each component and the cumulative temperature, which is an important parameter in this embodiment, will be described.

<3. Process Performed by Internal Oxidation Starting Temperature Estimation Unit>

As described above, the internal oxidation starting temperature Tcr is a minimum temperature required for the internal oxide layer to grow on a surface of the hot-rolled steel sheet. The inventors found that the internal oxidation starting temperature Tcr depended on the composition of the hot-rolled steel sheet, particularly, Si, Mn, and Al concentrations. In this embodiment, the Si, Mn, and Al concentrations are mass % of each component with respect to the total mass of a base metal. The concentrations of these components may be measured by a general analytical method. For example, these components may be measured using inductively coupled plasma-atomic emission spectrometry (ICP-AES). Therefore, the Si, Mn, and Al concentrations in this embodiment are average concentrations with respect to the entire hot-rolled steel sheet. The internal oxidation starting temperature estimation unit according to this embodiment estimates the internal oxidation starting temperature Tcr on the basis of the Si, Mn, and Al concentrations. When the internal oxidation starting temperature Tcr can be estimated, the cumulative temperature can be calculated on the basis of the internal oxidation starting temperature Tcr, and the thickness of the internal oxide layer can be estimated on the basis of the cumulative temperature. Hereinafter, an example of a method for estimating the internal oxidation starting temperature Tcr will be described, and any of tests may be performed offline.

(3-1. First Estimation Method)

In a first estimation method, the operator prepares a plurality of types of hot-rolled steel sheets in which the Si concentration, the Mn concentration, or the Al concentration or any combination thereof, preferably, the Si and Mn concentrations are different. The scale layers are formed on the surfaces of these hot-rolled steel sheets, and the internal oxide layers are not formed therein. For example, the hot-rolled steel sheet immediately after hot rolling (and before coiling) satisfies this condition. In addition, in a case in which the hot-rolled steel sheet is left in this state, there is a probability that an unintended internal oxide layer will be formed. Therefore, it is preferable to rapidly cool the hot-rolled steel sheet (at a temperature at which the internal oxide layer is clearly not formed, for example, at room temperature) immediately after hot rolling. The room temperature in this embodiment may be approximately 25° C.±5° C. For example, the rapid cooling may be performed by a method such as water cooling. The "rapid cooling" described below may be performed by the same method. This makes it possible to prepare a hot-rolled steel sheet in which an internal oxide layer is not formed on a surface of a base steel sheet (base metal) (even when the internal oxide layer is formed, the internal oxide layer which is so thin that it has little effect on the test is formed). Then, the operator heats these hot-rolled steel sheets under a condition in which the internal oxide layer can be formed, using a heating apparatus. Then, the temperature at which the internal oxide layer starts to be formed on the surface of the hot-rolled steel sheet may be set as the internal, oxidation starting temperature. The operator inputs the internal oxidation starting temperature to the processing device. The internal oxidation starting temperature estimation unit recognizes the input temperature as the internal oxidation starting temperature. That is, the internal oxidation starting temperature estimation unit sets the temperature at which the internal oxide layer starts to be formed on the surface of the hot-rolled steel sheet as the internal oxidation starting temperature, on the basis of the measured value of the thickness of the internal oxide layer formed in the hot-rolled steel sheet.

Here, it is, generally said that the internal oxide layer is formed in a state in which the scale layer is formed and the internal oxide layer is isolated from the outside air (atmosphere including oxygen). For example, when the coiled hot-rolled steel sheet (hereinafter, the hot-rolled steel sheet in this state is also simply referred to as a "coil") is cooled, the scale layer is formed on each portion to be measured in the hot-rolled steel sheet, and the portion to be measured is isolated from the outside air. Therefore, it is considered that the internal oxide layer is formed in a coil cooling step.

In addition, the isolation from the outside air can also be reproduced, for example, by placing the hot-rolled steel sheet, in which the scale layer has been formed, in anonoxidizing atmosphere. However, in some cases, the internal oxide layer is not formed only by simply heating the hot-rolled steel sheet in a non-oxidizing gas atmosphere (for example, a nitrogen gas atmosphere). For example, there is a case in which a space is formed between the scale layer and the base steel sheet due to a difference in constriction when the scale layer and the base steel sheet are cooled and the internal oxide layer is not formed. An example of the condition in which the internal, oxide layer can be formed is a condition in which the hot-rolled steel sheet is heated in a non-oxidizing gas+steam atmosphere. In this case, a dew point may be in a range of, for example, about −20° C. to +20° C.

The internal oxide layer is actually formed by the above-described operation. The inventors consider that the reason is that moisture entering (the space of) the interface between the scale layer and the base metal (base steel sheet) is reduced by Si. Mn, and Al in the base metal. That is, it is considered that Si, Mn, and Al in the base metal are oxidized by oxygen in the moisture and oxides thereof form the internal oxide layer. In addition, hydrogen (hydrogen gas) generated by the reduction of the moisture reduces iron oxide in the scale layer to generate moisture. This moisture is reduced by Si, Mn, and Al in the base metal, and the formation of the internal oxide layer proceeds.

Then, the operator heats the hot-rolled steel sheet at any retention temperature for one hour. Then, the operator rapidly cools the hot-rolled steel sheet to room temperature and measures the thickness of the internal oxide layer. For example, the hot-rolled steel sheet is cut in parallel in a thickness direction, and a cut surface is subjected to vital etching and is then observed with a scanning electron microscope+an energy dispersive X-ray spectrometer (SEM-EDS) or the like. In a region in which the internal oxide layer is formed, a metal oxide (grain boundary oxide) that is present at a grain boundary and a metal oxide (intragranular oxide) that is present within a crystal grain are observed. Therefore, in a case in which a precipitate in the cross section is analyzed by EDS, Si, Mn, or Al or any combination thereof is detected from the precipitate, and O is also detected at the same time, the precipitate is regarded as a metal oxide (grain boundary oxide). Then in a case in which metal oxides are observed at the grain boundary and in the crystal grain, this region is regarded as the internal oxide layer. Then, the distance from the surface of the base metal to the maximum depth of the internal oxide layer at each measurement point in the cross section (the number of measurement points is not limited, but, for example, three measurement points may be set) is measured, and an arithmetic average value of these distances is set as the thickness of the internal oxide layer. Then, the lowest retention temperature (that is, the temperature at which the internal oxide layer starts to be formed on the surface of the hot-rolled steel sheet) when the internal oxide layer is formed with an average thickness of, for example, about 1 to 2 μm may be set as the internal oxidation starting temperature. In addition, the temperature of the hot-rolled steel sheet may be measured using a thermocouple or the like. Further, here, it is assumed that the temperature of the hot-rolled steel sheet means the temperature of a base metal (base steel sheet) portion immediately below the scale layer. When the hot-rolled steel sheet is thin (for example, about 2 to 5 mm) and the temperature of the portion to be estimated is considered to be uniform in a sheet thickness direction, the temperature of the hot-rolled steel sheet may be the temperature of any portion in the sheet thickness direction or may be the temperature of a surface portion of the base metal. In a case in which the temperature fluctuates in the sheet thickness direction, it is preferable that the temperature of the hot-rolled steel sheet is the temperature of the surface of the base metal. In addition, from the viewpoint of measuring the thickness of the internal oxide layer as accurately as possible, it is preferable to heat the hot-rolled steel sheet to the retention temperature in as short a time as possible. Therefore, it is preferable that the heating speed is set to, for example, 10° C./sec (=600° C./min).

A condition in which the scale layer and the base metal are pressure-bonded in a non-oxidizing atmosphere is given as another example of the condition in which the internal oxide layer can be, formed. This is based on the assumption that the hot-rolled steel sheet in which the scale layer has been formed is coiled. In addition, even when a space is formed between the scale layer and the base steel sheet due to a difference in constriction during the cooling of the scale layer and the base steel sheet, the space can be removed, and the scale layer and the base steel sheet can be brought into close contact with each other. A pressure bonding method is not particularly limited. For example, the pressure bonding may be performed using a clamp or the like. A pressing force during the pressure bonding is not particularly limited. For example, in a case in which the clamp is tightened with a screw, a torque value during the tightening may be equal to or greater than 25 N·m. In this state, the hot-rolled steel sheet is heated to any retention temperature, and it is observed and determined whether or not the internal oxide layer is formed. A specific observation method and a specific determination method are as described above.

Still another example of the condition in which the internal oxide layer can be formed is a condition in which an iron oxide sample (for example, $Fe_3O_4$ powder) is interposed between a plurality of hot-rolled steel sheets (the hot-rolled steel sheets have the same composition) from which the scale layer and the internal oxide layer have been removed by mechanical grinding or the like and the hot-rolled steel sheets are pressure-bonded. A pressure bonding method is not particularly limited. For example, the pressure bonding may be performed using a clamp or the like. A pressing force during the pressure bonding is not particularly limited. For example, when a clamp is tightened with a screw, a torque value during the tightening may be equal to or greater than 25 N·m. In this state, the hot-rolled steel sheet is heated to any retention temperature, and it is observed and determined whether or not the internal oxide layer is formed. A specific observation method and a specific determination method are as described above. For example, data obtained by the above-described step is summarized as shown in Table 1. That is, the operator inputs the data to the processing device 10. Specific numerical values are not given in Table 1. However, when the composition of the hot-rolled steel sheet (particularly, the concentration of Si, Mn, or Al or any combination thereof) is different, the internal oxidation starting temperature is also different, which will be described below.

TABLE 1

| DATA | 1 | 2 | 3 | . . . |
|---|---|---|---|---|
| Tcr (° C) | . . . | . . . | . . . | . . . |
| Si (mass %) | . . . | . . . | . . . | . . . |
| Mn (mass %) | . . . | . . . | . . . | . . . |
| Al (mass %) | . . . | . . . | . . . | . . . |

Then, the internal oxidation starting temperature estimation unit 11 calculates a regression equation, using the calculated internal oxidation starting temperature as an objective variable and the Si concentration, the Mn concentration, or the Al concentration or any combination thereof of the hot-rolled steel sheet as an explanatory variable. For example, the regression equation is calculated by performing multiple regression analysis on the data summarized in Table 1. The regression equation indicates the correlation between the Si concentration, the Mn concentration, or the Al concentration or any combination thereof of the hot-rolled steel sheet and the estimated value of the internal oxidation starting temperature. The regression equation may include the Si concentration, the Mn concentration, or the Al concentration or any combination thereof as a variable. However, it is preferable that the regression equation includes the Si concentration and the Mn concentration among these concentrations as variables. It is more preferable that the regression equation includes all of the concentrations as variables. Furthermore, it is preferable to substitute the Si concentration or the Mn concentration or a combination thereof in the regression equation with a Si/Mn concentration ratio. An example of the regression equation is as follows.

$$Tcr(° \text{ C.})=s0+s1×(\% \text{ Si})+s2×(\% \text{ Mn})+s3×(\% \text{ Al}) \tag{A}$$

$$Tcr(° \text{ C.})=s0+s1×(\% \text{ Si})/(\% \text{ Mn})+s2×(\% \text{ Mn})+s3×(\% \text{ Al}) \tag{B}$$

$$Tcr(° \text{ C.})=s0+s1×(\% \text{ Si})+s2×(\% \text{ Mn}) \tag{C}$$

$$Tcr(° \text{ C.})=s0+s1×(\% \text{ Si})/(\% \text{ Mn})+s2×(\% \text{ Mn}) \tag{D}$$

In the regression equations (A) to (D), s0 to s3 are regression constants calculated by regression analysis, and element symbols indicate mass % of each element.

Then, the internal oxidation starting temperature estimation unit 11 determines the internal oxidation starting temperature Tcr on the basis of the calculated regression equation. Specifically, the operator measures the Si, Mn, and Al concentrations of the hot-rolled steel sheet that is actually manufactured and inputs these concentrations to the processing device 10. Then, the internal oxidation starting temperature estimation unit 11 substitutes the input values in the calculated regression equation to determine the internal oxidation starting temperature Thr.

(3-2. Second Estimation Method)

In a second estimation method, it is assumed that the hot-rolled steel sheet is coiled. Then, in the second estimation method, for each of a plurality of types of hot-rolled steel sheets in which the Si concentration, the Mn concentration, or the Al concentration or any combination thereof, preferably, the Si and Mn concentrations are different, a thickness-coiling temperature correlation graph indicating the correlation between a coiling completion temperature, which is a temperature at the time when the coiling of the hot-rolled steel sheet is completed, and the measured value of the thickness of the internal oxide layer is generated.

Specifically, the operator changes the coiling completion temperature of the hot-rolled steel sheet to any value and cools the hot-rolled steel sheet to room temperature. Then, the operator measures the thickness of the internal oxide layer for each coiling completion temperature. The coiling completion temperature, and a portion in which the thickness of the internal oxide layer is measured are not particularly limited. However, it is preferable that the portion is the center (center portion) of the hot-rolled steel sheet in the sheet width direction. The internal oxide layer formed in this portion tends to be particularly thick and has a high correlation with the cumulative temperature, which will be described in detail below. The coiling completion temperature may be actually measured using a thermocouple or a radiation-type thermometer that is installed immediately before a down coiler or may be derived by a simulation (heat conduction calculation) typified by, for example, Non-Patent Document 1. In a case in which the coiling completion temperature is actually measured by the thermocouple, the temperature of the base metal (base steel sheet) portion immediately below the scale layer may be measured. When the hot-rolled steel sheet is thin (for example, about 2 to 5 mm) and the temperature of the portion in which the coiling completion temperature is measured is considered to be uniform in the sheet thickness direction, the coiling completion temperature may be the temperature of any portion in the sheet thickness direction or may be the temperature of a surface portion of the base metal. In a case in which the temperature fluctuates in the sheet thickness direction, the coiling completion temperature is preferably the temperature of the surface of the base metal. In a case in which the radiation-type thermometer is used, the measured value of the radiation-type thermometer may be used as the coiling completion temperature without any change. The method for measuring the thickness of the internal oxide layer is as described above. However, the measurement portion may be, for example, a center portion at, a position that is 100 m away from the tip of the coil (an end portion on the innermost side in the coil).

Then, the operator inputs a plurality of measurement points obtained in the above-described process to the processing device 10. The internal oxidation starting, temperature estimation unit 11 generates a thickness-coiling temperature correlation graph from the input measurement points. An example of the thickness-coiling temperature correlation graph is shown in FIG. 1. In FIG. 1, a horizontal axis indicates the coiling completion temperature (° C.), and a vertical axis indicates the measured value ($\mu$m) of the thickness of the internal oxide layer. A point P10 indicates the measured values of the coiling completion temperature and the thickness of the internal oxide layer of the hot-rolled steel sheet having Si: 0.5 mass %, Mn: 2.3 mass %, and Al: 0.18 mass %. A graph L10 is a thickness-coiling temperature correlation graph corresponding to the point P10 and can be obtained by performing regression analysis on the point P10. In the example shown in FIG. 1, regression is performed by a quadratic function. The same applies to graphs L11 and L12 which will be described below.

A point P11 indicates the coiling completion temperature and the measured value of the thickness of the internal oxide layer of the hot-rolled steel sheet having Si: 0.6 mass %, Mn: 2.0 mass %, and Al: 0.03 mass %. A graph L11 is a thickness-coiling temperature correlation graph corresponding to the point P11 and is obtained by performing regression analysis on the point P11.

A point P12 indicates the coiling completion temperature and the measured value of the thickness of the internal oxide layer of the hot-rolled steel sheet having Si: 1.0 mass %, Mn: 2.3 mass %, and Al: 0.02 mass %. A graph L12 is a thickness-coiling temperature correlation graph corresponding to the point P12 and is obtained by performing regression analysis on the point P12.

As can be clearly seen from FIG. 1, even when the coiling completion temperature is the same, the thickness of the internal oxide layer varies depending on the composition of the hot-rotted steel sheet. In the second estimation, method, the internal oxidation starting temperature estimation unit 11 extrapolates the thickness-coiling temperature correlation graph to calculate, as the internal oxidation starting temperature, the coiling completion temperature when the thickness of the internal oxide layer is zero. In the example shown in FIG. 1, the internal oxidation starting temperature Tcr of the hot-rolled steel sheet having Si: 1.0 mass %, Mn: 2.3 mass %, and Al: 0.02 mass % was the lowest temperature of 461° C., the internal oxidation starting temperature Tcr of the hot-rolled steel sheet having Si: 0.5 mass %, Mn: 2.3 mass %, and Al: 0.18 mass % was the second lowest temperature of 467° C., and the internal, oxidation starting temperature Tcr of the hot-rolled steel sheet having Si: 0.6 mass %, Mn: 2.0 mass %, and Al: 0.03 mass % was the highest temperature of 481° C. As can be seen from the above, the internal oxidation starting temperature Tcr also varies depending on the composition of the hot-rolled steel sheet (particularly, the Si concentration, the Mn concentration, or the Al concentration or any combination thereof). The internal oxidation starting temperature estimation unit 11 summarizes the data obtained by the above-described step as shown in, for example, Table 1.

In addition, a coiling test performed by the second estimation method is basically performed using an actual machine. However, this test may be substituted with the test given as the second example of the first estimation method (the test in which the scale layer and base metal are pressure-bonded in the non-oxidizing atmosphere). In this case, the operator considers the retention temperature as the coiling completion temperature and measures the thickness of the internal oxide layer for a plurality of retention temperatures. Then, the internal oxidation starting temperature estimation unit 11 generates a thickness-coiling temperature correlation graph in the same manner as described above. Then, the internal oxidation starting temperature estimation unit 11 extrapolates the thickness-coiling temperature correlation graph and calculates, as the internal oxidation starting temperature, the coiling completion temperature when the thickness, of the internal oxide layer is zero.

Then, the internal oxidation starting temperature estimation unit 11 calculates a regression equation, using the calculated internal oxidation starting temperature as an objective variable and the Si concentration, the Mn concentration, or the Al concentration or any combination thereof of the hot-rolled steel sheet as an explanatory variable. A method for calculating the regression equation is as described above. For example, the regression equations (A) to (D) can be calculated.

Then, the internal oxidation starting temperature estimation unit 11 determines the internal oxidation starting temperature Tcr on the basis of the calculated regression equation. Specifically, the operator measures the Si, Mn, and Al concentrations of the hot-rolled steel sheet that is actually manufactured and inputs these concentrations to the processing device 10. Then, the internal oxidation starting temperature estimation unit 11 substitutes the input values in the calculated regression equation to determine the internal oxidation starting temperature Tcr.

(3-3. Third Estimation Method)

In a third estimation method, the internal oxidation starting temperature Tcr which is an objective variable is determined such that the correlation between the cumulative temperature and the measured value of the thickness of the internal oxide layer when the internal oxidation starting temperature Tcr is changed as a variable parameter is the highest. Here, as described above, the cumulative temperature is a parameter that has a very high correlation with the thickness of the internal oxide layer. Therefore, first, the cumulative temperature will be described.

(3-3-1. Cumulative Temperature)

The cumulative temperature is represented by the following Expression (1).

$$S_T = \int_{t0}^{t1} (T - Tcr)dt \qquad (1)$$

In Expression (1) $S_T$ is the cumulative temperature and has a value of $S_T \geq 0$. T is the temperature of the portion to be estimated, in which the thickness of the internal oxide layer is to be estimated, in the hot-rolled steel sheet, Tcr is the internal oxidation starting temperature, t0 is an estimation start time when the estimation of the thickness of the internal oxide layer is started, and t1 is an estimation evaluation time. In the integration interval in which T−Tcr is equal to or less than 0. T Tcr is set to 0. That is, in addition, for example, the thickness of the internal oxide layer is estimated by the following Expression (2), which will be described in detail below.

$$H = \alpha \times S_T + H_0 \qquad (2)$$

In Expression (2), H is (the estimated value of) the thickness of the internal oxide layer, $\alpha$ is a proportional constant, $S_T$ is the cumulative temperature, and $H_0$ is an initial value of the thickness of the internal oxide layer. Therefore, it can be said that Expression (2) is an expression indicating the correlation between the cumulative temperature and the estimated value of the thickness of the internal oxide layer. Since the cumulative temperature has a very high correlation with the thickness of the internal oxide layer, it is possible to estimate the thickness of the internal oxide layer with high accuracy, which will be described in detail below.

Therefore, the cumulative temperature is a very important parameter in this embodiment. The cumulative temperature is represented by the above-described Expression (1) Therefore, each parameter constituting the cumulative temperature will be described in detail.

T is the temperature of the portion to be estimated, in which the thickness of the internal oxide layer is to be estimated, in the hot-rolled steel sheet. Here, the scale layer is formed in the hot-rolled steel sheet. Therefore, here, it is assumed that the "temperature of the portion to be estimated" means the temperature of the base metal (base steel sheet) portion immediately below the scale layer. When the hot-rolled steel sheet is thin (for example, about 2 to 5 mm) and the temperature of the portion to be estimated is considered to be uniform in the sheet thickness direction, the temperature of the portion to be estimated may be the temperature of any portion in the sheet thickness direction or may be the temperature of the surface portion of the base metal. In a case in which the temperature fluctuates in the sheet, thickness direction, it is preferable that the temperature of the portion to be estimated is the temperature of the surface of the base metal. The temperature of the portion to be estimated may be actually measured using a thermocouple or the like (in this case, the operator may input an output value of the thermocouple to the processing device 10. The internal oxidation starting temperature estimation unit 11 recognizes the input temperature as the temperature of the portion to be estimated). For example, the temperature may be derived by the simulation (heat conduction calculation) typified by Non-Patent Document 1 (in this case, the internal oxidation starting temperature estimation unit 11 may perform the simulation). In this simulation, the thermal history of the hot-rolled steel sheet described above is taken into consideration.

Tcr is the internal oxidation starting temperature (in this estimation method, the internal oxidation starting temperature is first set to any value, which will be described in detail below). Therefore, the cumulative temperature is a value obtained by integrating the difference between the temperature T of the portion to be estimated and the internal oxidation starting temperature Tcr over time. In this embodiment, it is considered, that the internal oxide layer is formed (or grows) in a case in which the temperature of the portion to be estimated exceeds the internal oxidation starting temperature Tcr. Conversely, in a case in which the temperature of the portion to be estimated is equal to or lower than the internal oxidation starting temperature Tcr, the internal oxide layer is not formed (in a case in which the internal oxide layer has already been formed, the growth thereof stops). The internal oxidation starting temperature Tcr is a constant unique to the kind of steel. Therefore, an appropriate internal oxidation starting temperature Tcr is given to the steel material to which the invention is applied. A specific giving method will be described below.

t0 is the estimation start time when the estimation of the thickness of the internal oxide layer is started. The estimation start time is set to any time in the process in which the internal oxide layer is assumed to be formed. As described above, it is generally said that the internal oxide layer is formed in a state in which the scale layer is formed and the internal oxide layer is isolated from the outside air (atmosphere including oxygen). For example, when the coiled hot-rolled steel sheet (that is a coil) is cooled, the scale layer is formed in each portion to be measured in the hot-rolled steel sheet, and the portion to be measured is isolated from the outside air. Therefore, it is considered that the internal oxide layer is formed in a coil cooling step. Then, the coil cooling step is started from the coiling completion time of the hot-rolled steel sheet. Therefore, the estimation start time to may be regarded as the coiling completion time of the hot-rolled steel sheet. Of course, the estimation start time to may be set to any time during the cooling step. In a case in which annealing or the like is performed during the cooling step, the estimation start time t0 may be set to a time period for which the annealing or the like is performed. For example, an annealing start time (the time when the portion to be estimated in the hot-rolled steel sheet reaches an inlet of an annealing furnace) may be set as the estimation start time t0, or a time in the middle of annealing may be set as the estimation start time t0. In addition, as described above, in the cooling step, there may be an integration interval in which the temperature T of the portion to be estimated is lower than the internal oxidation starting temperature Tcr. In this case, for example, the portion to be estimated is cooled, to the internal oxidation starting temperature Tcr or lower during the cooling step, and the portion to be estimated is reheated to the internal oxidation, starting temperature Tcr or higher by the annealing.

t1 is the estimation evaluation time. Therefore, it can be said that the internal oxide layer thickness estimation unit 12 according to this embodiment estimates the thickness of the internal oxide layer at the estimation evaluation time t1 The estimation evaluation time t1 is set to a time after the estimation start time t0. For example, any time during the coil cooling step may be set as the estimation evaluation time t1. Specifically, in a case in which annealing or the like is performed during the coil cooling step, the time when the annealing ends (the time when the portion to be estimated in the hot-rolled steel sheet reaches an outlet of the annealing furnace) may be set as the estimation evaluation time t1, or a time during the annealing may be set as the estimation evaluation time t1. Furthermore, any time during the cooling step after the annealing ends may be set as the estimation evaluation time t1. In this case, the time when the tempera-
ture T of the portion to be estimated finally reaches the
internal oxidation starting temperature Tcr (after all of the
above-described annealing and the like are performed) in the
coil cooling step may be set as the estimation evaluation
time t1. A time thereafter (that is, the time when the
temperature T of the portion to be estimated is further
cooled) may be set as the estimation evaluation time t1. As
described above, in an integration interval after the tempera-
ture T of the portion to be estimated, reaches the internal
oxidation starting temperature Tcr, T−Tcr is equal to or less
than 0. However, since T−Tcr is 0 in this integration interval,
there is no effect on the accuracy of estimation.

In the calculation of the cumulative temperature, the
temperature T of the portion to be measured may be actually
measured or may be calculated by a simulation considering
the thermal history of the hot-rolled steel sheet. In the former
case, the operator may input the measured value to the
processing device 10. In the latter case, the internal oxida-
tion starting temperature estimation unit 11 may perform the
simulation. In the calculation of the cumulative temperature,
the internal oxidation starting temperature Tcr is first set to
any value, which will be described in detail below. In a case
in which T−Tcr is equal to or less than 0 in any of the
integration intervals, T−Tcr is set to 0 in the integration
interval. In addition, in the integration operation, the inte-
gration interval (t0 to t1) may be divided into minute
intervals Δt, and the discrete values of the cumulative
temperatures in each interval Δt may be summed to calculate
the cumulative temperature. The operator may input t0 and
t1 to the processing device 10. The internal oxidation
starting temperature estimation unit 11 recognizes the input
values as t0 and t1 in Expression (1). Alternatively, t0 and t1
may be preset, as specified values.

In the third estimation method, the internal oxidation
starting temperature estimation unit 11 estimates the internal
oxidation starting temperature Tcr using the cumulative
temperature. First, the internal oxidation starting tempera-
ture estimation, unit 11 sets the internal oxidation starting
temperature Tcr to any value (for example, any value in a
range of 200° C. to 1000° C.). Then, the portions to be
measured are set at a plurality of positions on the surface of
the hot-rolled steel sheet, and the cumulative temperatures of
these portions to be measured are calculated on the basis of
the above-described Expression (1). The portion to be mea-
sured may be set by the internal oxidation starting tempera-
ture estimation unit 11 or by the operator. In the former case,
the internal oxidation starting temperature estimation unit 11
may display the portion to be measured on a display or the
like. In the latter, case, the operator may input the portion to
be measured to the processing device 10. The setting of the
portion to be measured may be performed for the total length
of the hot-rolled steel sheet in a rolling direction and the total
width of the hot-rolled steel sheet in the sheet width direc-
tion or may be performed for a part of the total length and
the total width. In an example described below, the portion
to be measured is set for the total length and the total width.
In addition, it is preferable that the portion to be measured
is set in a sheet width center quarter portion. The reason is
that the cumulative temperature in the sheet width center
quarter portion has a high correlation with the measured
value of the thickness of the internal oxide layer, which will
be described below. Here, the sheet width center quarter
portion means a region in a range from the center (center
portion) of the hot-rolled steel sheet in the sheet width
direction to portions (quarter portions) which are ¼ of the
sheet width away from the center toward both ends in the sheet width direction (that is, a region interposed between a
quarter portion close to one end portion in the width direc-
tion and a quarter portion close to the other end portion).

Meanwhile, the operator actually measures the thickness
of the internal oxide layer in the portion to be measured and
inputs the measured thickness to the processing device 10.
A method for measuring the thickness of the internal oxide
layer is as described above. In this way, the cumulative
temperature and the measured value of the thickness of the
internal oxide layer are obtained for the plurality of portions
to be measured. In addition, this test may be performed as an
offline test.

Figure 2:
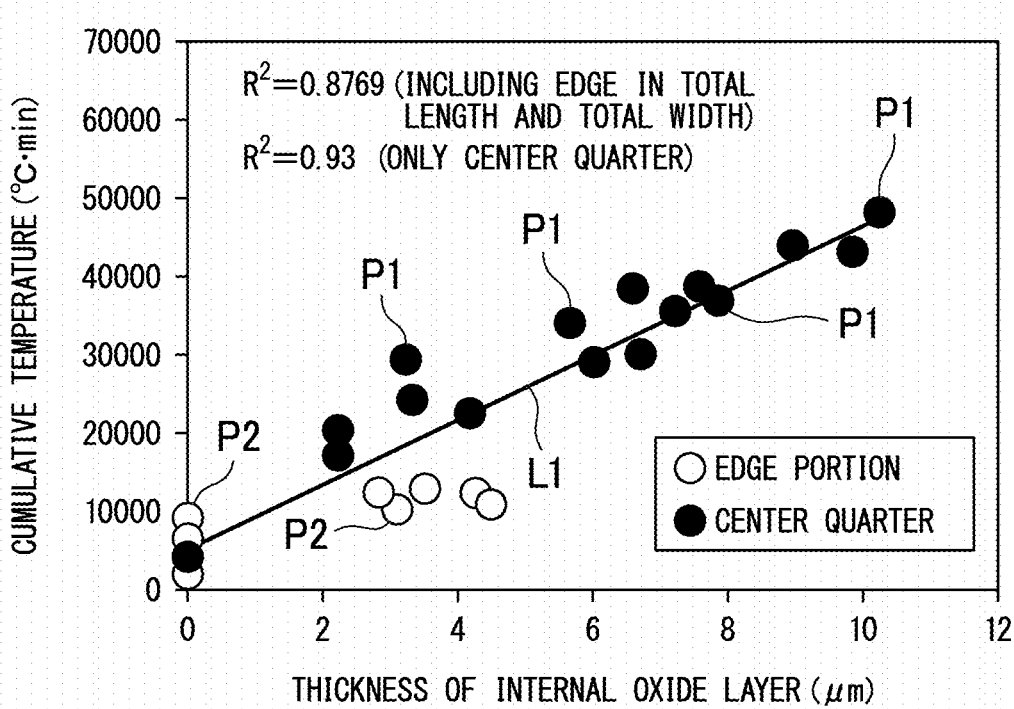
FIG. 2 is a graph showing a correlation between the measured value of the thickness of the internal oxide layer and a cumulative temperature.

Then, the internal oxidation starting temperature estima-
tion unit 11 plots the obtained cumulative temperature and
the obtained measured value of the thickness of the internal
oxide layer as measurement points on the xy plane having
the cumulative temperature and the thickness of the internal
oxide layer as the x-axis and the y-axis. An example is
shown in FIG. 2. In FIG. 2, the horizontal axis indicates the
thickness (μm) of the internal oxide layer, and the vertical
axis indicates the cumulative temperature (° C. min). In this
example, the internal oxidation starting temperature Tcr is
500° C. Points P1 and P2 indicate the cumulative tempera-
ture and the measured value of the thickness of the internal
oxide layer for each portion to be measured. The point P1
indicates the value of the portion to be measured set in the
sheet width center quarter portion of the hot-rolled steel
sheet, and the point P2 indicates the value of the portion to
be measured set in the edge portion (end portion) of the
hot-rolled steel sheet in the sheet width direction.

Then, the internal oxidation starting temperature estima-
tion unit 11 performs regression analysis on the plurality of
measurement points to calculate an approximate expression
(temperature-determining correlation expression) of these
measurement points. The regression analysis may be, for
example, simple regression analysis using a least-square
method. Here, it is preferable that the portion to be measured
is set in the sheet width center quarter portion. This is
because the cumulative temperature and the measured value
of the thickness of the internal oxide layer in the sheet width
center quarter portion have a high correlation. Furthermore,
the internal oxide layer is likely to be formed particularly
thickly in the sheet width center quarter portion, particularly,
in the center portion. In this respect, it is preferable that the
portion to be measured is set in the sheet width center
quarter portion. In the example shown in FIG. 2, the internal
oxidation starting temperature estimation unit 11 performs
simple regression analysis on the measurement point P1
(sheet width center quarter portion) to obtain a graph L1
(temperature-determining correlation expression). A degree-
of-freedom determination coefficient $R^2$ of the graph L1 is
0.93. In the example shown in FIG. 2, in a case in which
regression analysis is collectively performed on groups of
the measurement points P1 and P2 (edge portion), the
degree-of-freedom determination coefficient $R^2$ of the tem-
perature-determining correlation expression is approxi-
mately 0.88. In the edge portion, a decrease in temperature
is more remarkable than that in the sheet width center
quarter portion, and unevenness is also larger than that in the
sheet width center quarter portion. Therefore, in the edge
portion, it is considered that the correlation between the
cumulative temperature and the measured value of the
thickness of the internal oxide layer is slightly low. That is,
in a case in which the regression analysis is performed
including the cumulative temperature of the edge portion, the degree-of-freedom determination coefficient $R^2$ of the temperature-determining correlation expression is slightly small.

Then, the internal oxidation starting temperature estimation unit 11 determines the internal oxidation starting temperature Tcr on the basis of the correlation between, the cumulative temperature and the measured value of the thickness of the internal oxide layer when the internal oxidation starting temperature Tcr is changed. For example, the internal oxidation starting temperature estimation unit 11 derives the above-described temperature-determining correlation expression, using various different values of the internal oxidation starting temperature Tcr, and calculates each degree-of-freedom determination coefficient $R^2$. Then, the internal oxidation starting temperature estimation unit 11 selects the internal oxidation starting temperature Tcr when the degree-of-freedom determination coefficient $R^2$ of the temperature-determining correlation expression has the largest value (that is, the correlation between the cumulative temperature and the measured value of the thickness of the internal oxide layer is the highest).

Figure 3:
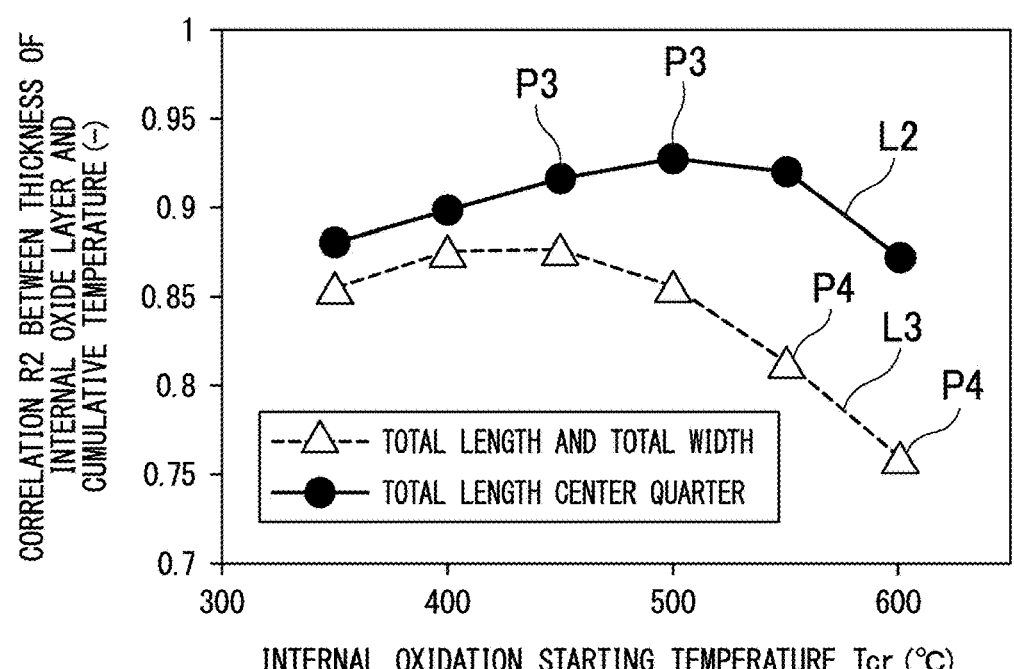
FIG. 3 is a graph showing that the correlation between the measured value of the thickness of the internal oxide layer and the cumulative temperature fluctuates depending on an internal oxidation starting temperature Tcr.

FIG. 3 shows a specific example of the above and is a graph showing that the degree-of-freedom determination coefficient $R^2$ (that is, the correlation between the cumulative temperature and the measured value of the thickness of the internal oxide layer) of the temperature-determining correlation expression fluctuates depending on the internal oxidation starting temperature Tcr. In FIG. 3, the horizontal axis indicates the internal oxidation starting temperature Tcr(° C.), and the vertical axis indicates the degree-of-freedom determination coefficient $R^2$ of the temperature-determining correlation expression. Groups of plotted points P3 and P4 are points corresponding to the internal oxidation starting temperature Thr and the degree-of-freedom determination coefficient R of the temperature-determining correlation expression, and graphs L2 and L3 are curve, graphs connecting the points P3 and P4, respectively. However, the point P3 indicates the degree-of-freedom determination coefficient $R^2$ of the temperature-determining correlation expression obtained by performing regression analysis on the cumulative temperature in the sheet width center quarter portion (the sheet width center quarter portion in the total length), and the point P4 indicates the degree-of-freedom determination coefficient $R^2$ of the temperature-determining correlation expression obtained by performing regression analysis on the cumulative temperatures in the sheet width center quarter portion and the edge portion (the total length and the total width). As can be clearly seen from FIG. 3 the degree-of-freedom determination coefficient $R^2$ indicated by the point P3 is larger than the degree-of-freedom determination coefficient $R^2$ indicated by the point P4. Therefore, the cumulative temperature in the sheet width center quarter portion has a high, correlation with the measured value of the thickness of the internal oxide layer.

Both the graphs L2 and L3 have a peak. The graph L2 has a peak at an internal oxidation starting temperature Tcr of 500° C., and the graph L3 has a peak at an internal oxidation starting temperature Tcr of 450° C. The temperature of the edge portion is lower than the temperature of the sheet width center quarter portion, and unevenness is also large. Therefore, it is considered that this tendency appears. In any case, the peak of the graph L3 is lower than the peak of the graph L2. Therefore, as can be seen from the example shown in FIG. 3, it, is preferable to set the internal oxidation starting temperature Tcr to 500° C.

The operator and the internal oxidation starting temperature estimation unit 11 perform the above-described process on each of a plurality of types of hot-rolled steel sheets in which the Si concentration, the Mn concentration, or the Al concentration or any combination thereof, preferably, the Si and Mn concentrations are different to calculate the internal oxidation starting temperature Tcr as an objective variable. Then, the internal oxidation starting temperature estimation unit 11 calculates a regression equation, using the calculated internal oxidation starting temperature as an objective variable and the Si concentration, the Mn concentration, or the Al concentration or any combination thereof of the hot-rolled steel sheet as an explanatory variable. A method for calculating the regression equation is as described above. For example, the regression equations (A) to (D) can be calculated.

Then, the internal oxidation starting temperature estimation unit 11 determines the internal oxidation starting temperature Tcr on the basis of the calculated regression equation. Specifically, the operator measures the Si concentration, the Mn concentration, and the Al concentration of the hot-rolled steel sheet that is actually manufactured and inputs the measured concentrations to the processing device 10. Then, the internal oxidation starting temperature estimation unit 11 substitutes these concentrations in the calculated regression equation to determine the internal oxidation starting temperature Tcr.

(3-4. Fourth Estimation Method)

A fourth estimation method is similar to the third estimation method, but is different from the third estimation method in that a quadratic function of the cumulative temperature (a linear function in the third estimation method) is applied to the measured value of the thickness of the internal oxide layer.

Specifically, first, the internal, oxidation starting temperature estimation unit 11 sets the internal oxidation starting temperature Tcr to any value (for example, any value in a range of 200 to 1000° C.). Then, the internal oxidation starting temperature estimation unit 11 sets the portions to be measured at a plurality of positions on the surface of the hot-rolled steel sheet and calculates the cumulative temperature of these portions to be measured on the basis of the above-described Expression (1). The portion to be measured may be set by the internal oxidation starting temperature estimation unit 11 or by the operator. In the former case, the internal oxidation starting temperature estimation unit 11 may display the portion to be measured on a display or the like. In the latter case, the operator may input the portion to be measured to the processing device 10. The setting of the portion to be measured may be performed for the total length of the hot-rolled steel sheet in the rolling direction and the total width of the hot-rolled steel sheet in the sheet width direction or may be performed for a part of the total length, and the total width. In an example described below, the portion to be measured is set for the total length and the total width. In addition, it is preferable that the portion to be measured is set in a sheet width center quarter portion. This is because the cumulative temperature in the sheet width center quarter portion has a high correlation with the measured value of the thickness of the internal oxide layer as described above. The definition of the sheet width center quarter portion is as described above.

Meanwhile, the operator actually measures the thickness of the internal oxide layer in the portion to be measured. A method for measuring the thickness of the internal oxide layer is as described above. In this way, the internal oxidation starting temperature, estimation unit 11 obtains the cumulative temperature and the measured value of the thickness of the internal oxide layer for the plurality of portions to be measured. In addition, this test may be performed as an offline test.

Then, the internal oxidation starting temperature estimation unit 11 plots the obtained cumulative temperature and, the obtained measured value of the thickness of the internal oxide layer as measurement points on the xy plane having the cumulative temperature and the thickness of the internal oxide layer as the x-axis and the y-axis.

Then, the internal oxidation starting temperature estimation unit 11 performs regression analysis on the plurality of measurement points using the quadratic function of the cumulative temperature to calculate an approximate expression (temperature-determining correlation expression) of the plurality of measurement points. The regression analysis may be, for example, simple regression analysis using a least-square method. Here, it, is preferable that the portion to be measured is set in the sheet width center quarter portion. This is because the cumulative temperature and the measured value of the thickness of the internal oxide layer in the sheet width center quarter portion have a high correlation. Furthermore, the internal oxide layer is likely to be formed particularly thickly in the sheet width center quarter portion, particularly, in the center portion. In this respect, it is preferable that the portion to be measured is set in the sheet width center quarter portion. Then, the internal oxidation starting temperature estimation unit 11 applies the quadratic function of the cumulative temperature to the measured value of the thickness of the internal oxide layer to calculate the sum of squared deviations.

Then, the internal oxidation starting temperature estimation unit 11 performs the same process while changing the internal oxidation starting temperature Tcr as a variable parameter to determine the internal oxidation starting temperature Tcr such that the sum of squared deviations when the quadratic function of the cumulative temperature is applied to the measured value of the thickness of the internal oxide layer is minimized.

The operator and the internal oxidation starting temperature estimation unit 11 perform the above-described process on each of a plurality of types of hot-rolled steel sheets in which the Si concentration, the Mn concentration, or the Al concentration or any combination thereof, preferably, the Si and Mn concentrations are different to calculate the internal oxidation starting temperature Tcr as an objective variable. Then, the internal oxidation starting temperature estimation unit calculates a regression equation, using the calculated internal oxidation starting temperature as an objective variable and the Si concentration, the Mn concentration, or the Al concentration or any combination thereof of the hot-rolled steel sheet as an explanatory variable. A method for calculating the regression equation is as described above. For example, the regression equations (A) to (D) can be calculated.

Then, the internal oxidation starting temperature estimation unit 11 determines the internal oxidation starting temperature Tcr on the basis of the calculated regression equation. Specifically, the operator measures the Si concentration, the Mn concentration, and the Al concentration of the hot-rolled steel sheet that is actually manufactured and substitutes these concentrations into the regression equation calculated above to determine the internal oxidation starting temperature Tcr.

<4. Process Performed by Internal Oxide Layer Thickness Estimation Unit>

Next the process performed by the internal oxide layer thickness estimation unit 12 according to this embodiment will be described. The internal oxide layer thickness estimation unit 12 according to this embodiment estimates the thickness of the internal oxide layer on the basis of the internal oxidation starting temperature estimated by the internal oxidation starting temperature estimation unit 11 and the following Expression (2).

$$H=\alpha \times S_T + H_0 \qquad (2)$$

In Expression (2), $S_T$ is the cumulative temperature, and $H_0$ is the initial value of the thickness of the internal oxide layer. The initial value $H_0$ of the thickness of the internal oxide layer means the thickness of the internal oxide layer at the estimation start time t0. The operator can rapidly cool the hot-rolled steel sheet to the internal oxidation starting temperature Tcr or lower at the estimation start time t0 and then observe a cross section to measure the initial value $H_0$ of the thickness of the internal oxide layer. When it is clear that the internal oxide layer is not formed at the estimation start time t0, this measurement may not be performed, and the initial value $H_0$ may be set to 0.

$\alpha$ is a proportional constant. The internal oxide layer thickness estimation unit 12 can determine the proportional constant $\alpha$ using regression analysis on the basis of a plurality of sets of measured data of the cumulative temperature and the measured value, of the thickness of the internal oxide layer. However, the proportional constant $\alpha$ may be calculated by a method which will be described below.

Specifically, the operator prepares a plurality of types, of hot-rolled steel sheets in which the Si concentration, the Mn concentration, or the Al concentration or any combination thereof, preferably, the Si and Mn concentrations are different. Then, these hot-rolled steel sheets are coiled and then held at a predetermined retention temperature. The retention temperature is not particularly limited, but is preferably, for example, about 600 to 700° C. This is because an internal oxidation phenomenon is remarkable in this temperature range.

Then, the operator actually measures the thickness of the internal oxide layer whenever a preset retention time elapses. A method for measuring the thickness of the internal oxide layer is as described above. In addition, the position where the thickness of the internal oxide layer is actually measured is not particularly limited, but is preferably for example, the center (center portion) of the hot-rolled steel sheet in the sheet width direction. Data obtained by the above-described step is summarized in, for example, Table 2. The data in Table 2 is created for each of the prepared hot-rolled steel sheets. The operator inputs the data in Table 2 to the processing device 10. In Table 2, Δt is the retention time (elapsed time after the temperature of the coil reaches the retention temperature), and H is the thickness of the internal oxide layer. It is preferable to acquire five or more data items for each hot-rolled steel sheet. This is to estimate the proportional constant $\alpha$ with high accuracy.

TABLE 2

| DATA | 1 | 2 | 3 | . . . |
|------|---|---|---|-------|
| Δt (min) | . . . | . . . | . . . | . . . |
| H (μm) | . . . | . . . | . . . | . . . |

Figure 4:
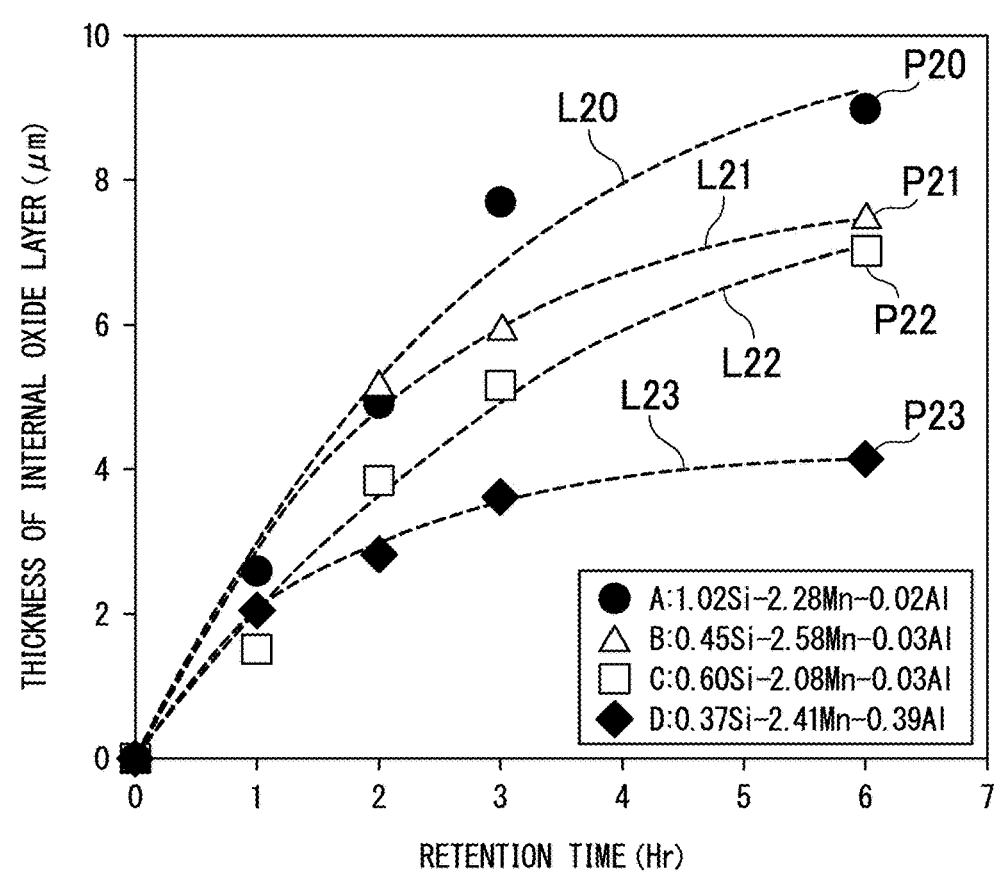
FIG. 4 is a graph showing a correlation between a retention time when the hot-rolled steel sheet is held at 600° C. and the thickness of the internal oxide layer for each composition of the hot-rolled steel sheet.

FIG. 4 shows an example in which the data in Table 2 is graphed. In FIG. 4, the horizontal axis indicates the retention time (hr), and the vertical axis indicates the measured value μm) of the thickness of the internal oxide, layer. A point P20 indicates the retention time and the measured value of the thickness of the internal oxide layer in the hot-rolled steel sheet having Si: 1.02 mass %, Mn: 2.28 mass %, and Al: 0.02 mass %. A graph L20 is an approximate curve of the point P20.

A point P21 indicates the retention time and the measured value of the thickness of the internal oxide layer in the hot-rolled steel sheet having Si: 0.45 mass %, Mn: 2.58 mass %, and Al: 0.03 mass %. A graph L21 is an approximate curve of the point P21.

A point P22 indicates the retention time and the measured value of the thickness of the internal oxide layer in the hot-rolled steel sheet having Si: 0.60 mass %, Mn: 2.08 mass %, and Al: 0.03 mass %. A graph L22 is an approximate curve of the point P22.

A point P23 indicates the retention time and the measured value of the thickness of the internal oxide layer in the hot-rolled steel sheet having Si: 0.37 mass %, Mn: 2.41 mass %, and Al: 0.39 mass %. A graph L23 is an approximate curve of the point P23.

As can be clearly seen from FIG. 4, the proportional constant $\alpha$ varies depending on the composition of the hot-rolled steel sheet.

Since the retention temperature is constant, Expressions (1) and (2) are substituted with the following Expression (3).

$$H=\alpha(Te-Tcr)\Delta t \qquad (3)$$

In Expression (3), Te is the retention temperature, and $\Delta t$ is the retention time.

Therefore, the internal oxide layer thickness estimation unit 12 can perform simple regression analysis on the data in Table 2 to calculate the proportional constant $\alpha$ for each hot-rolled steel sheet. A value determined by the above-described method may be used, as the internal oxidation starting temperature Tcr in Expression (3). For example, for a kind of steel A corresponding to the point P20 in FIG. 4, data shown in the following Table 3 is obtained.

TABLE 3

| DATA | 1 | 2 | 3 | 4 | 5 |
|---|---|---|---|---|---|
| Te (° C.) | 600 | 600 | 600 | 600 | 600 |
| Tcr (° C.) | 461 | 461 | 461 | 461 | 461 |
| Δt (min) | 0 | 60 | 120 | 180 | 360 |
| H (μm) | 0 | 2.56 | 4.81 | 7.69 | 8.97 |

When simple regression analysis is performed on the data in Table 3, a linear intercept of 1.27 and a slope of $1.78 \times 10^{-4}$ are obtained. Therefore, the proportional constant $\alpha$ corresponding to the kind of steel A is $\Delta=1.78 \times 10^{-4}$ μm/(° C.·min). The internal oxide layer thickness estimation unit 12 summarizes the data obtained by the above-described step as shown in, for example, Table 4.

TABLE 4

| DATA | 1 | 2 | 3 | . . . |
|---|---|---|---|---|
| α(μm/(° C. · min)) | . . . | . . . | . . . | . . . |
| Si (mass %) | . . . | . . . | . . . | . . . |
| Mn (mass %) | . . . | . . . | . . . | . . . |
| Al (mass %) | . . . | . . . | . . . | . . . |

Then, the internal oxide layer thickness estimation unit 12 measures the cumulative temperature of the portion to be measured, in which the thickness of the internal oxide layer is desired to be known, on the basis of Expression (1). The temperature T of the portion to be measured may be measured by the above-described simulation or actual measurement. Furthermore, the internal oxidation starting temperature Tcr estimated by the above-described method is used. Then, the internal oxide layer thickness estimation unit 12 can apply the measured cumulative temperature to Expression (2) to, estimate the thickness of the internal oxide layer in the portion. Here, the internal oxide layer thickness estimation unit 12 may use, as the proportional constant $\alpha$ in Expression (2), a proportional constant $\alpha$ which corresponds to a composition closest to the composition of the hot-rolled steel sheet to be measured in the data summarized in Table 4. Alternatively, the internal oxide layer thickness estimation unit 12 can determine the proportional constant $\alpha$ with regression analysis on the basis of a plurality of sets of measured data of the cumulative temperature and the measured value of the thickness of the internal oxide layer as described above. There is a high correlation between the cumulative temperature and the measured value of the thickness of the internal oxide layer, and the degree-of-freedom determination coefficient $R^2$ in Expression (2) is also large, which will be described in detail in examples. Therefore, it is possible to estimate the thickness of the internal oxide layer with high accuracy on the basis of Expression (2). Furthermore, the internal oxidation starting temperature Tcr fluctuates depending on the Si, Mn, and Al concentrations of the hot-rolled steel sheet. Therefore, in this embodiment, the internal oxidation starting temperature estimation unit 11 determines (estimates) the internal oxidation starting temperature Tcr on the basis of these concentrations. Therefore, it is possible to determine the internal oxidation starting temperature Tcr with high accuracy and thus to estimate the thickness of the internal oxide layer with high accuracy. The internal oxidation starting temperature is estimated with high accuracy, which makes it possible to improve the estimation accuracy of the thickness of the internal oxide layer and to determine appropriate manufacturing conditions. Specifically, a coiling temperature condition in which the thickness of the internal oxide layer after cooling is equal to or less than a predetermined value from coiling is optimized, and the efficiency of a pickling step which is the next step is improved.

In addition, since the cumulative temperature fluctuates depending on, for example, the coiling completion temperature, the thickness of the internal oxide layer also fluctuates. Therefore, the internal oxide layer thickness estimation unit 12 can also estimate the coiling completion temperature for obtaining a desired thickness of the internal oxide layer. In other words, the thickness of the internal oxide layer can be controlled by the coiling completion temperature.

<5. Procedure of Process Performed by Processing Device>

Figure 7:
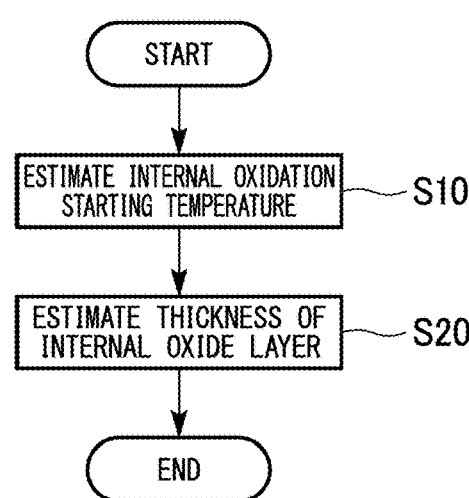
FIG. 7 is a flowchart showing, a flow of a process of the processing device according to this embodiment.

Next, a procedure of a process performed by the processing device according to this embodiment will be described with reference to a flowchart shown in FIG. 7. In addition, since the detailed process is as described above, only an outline will be described here.

In Step S10, the internal oxidation starting temperature estimation unit 11 estimates the internal oxidation starting temperature on the basis of the concentrations of Si Mn, and Al included in the hot-rolled steel sheet. Specifically, the internal oxidation starting temperature estimation unit 11 estimates the internal oxidation starting temperature on the basis of any of the first to fourth estimation methods.

In Step S20, the internal oxide layer thickness estimation unit 12 estimates the thickness of the internal oxide layer on the basis of the internal oxidation starting temperature estimated by the internal oxidation starting temperature estimation unit 11 and the above-described Expression (2).

EXAMPLES

Next, an example of this embodiment will be described. In this example, the following experiments were performed in order to check the effect of this embodiment. Of course, the invention is not limited to the example described below. It is obvious that those skilled in the art to which the invention belongs can conceive of various changes or modification examples within the scope of the technical idea described in the claims. Of course, it is understood that these also fall within the technical scope of the invention.

First, kinds of steel A to D shown in Table 5 were prepared as test pieces for hot-rolled steel sheets. Then, each of the kinds of steel A to D was coiled at a coiling completion temperature of 600° C. and then air-cooled to room temperature. In this case, the internal oxidation starting temperature Tcr of the kinds of steel A to D was determined by the second estimation method. This result is also shown in Table 5. Then, multiple regression analysis was performed on the data in Table 5 to calculate the following regression equations (A1) and (B1).

$$Tcr=813.65\times143.4\times(\% \text{ Si})-118.63\times(\% \text{ Mn})+ \\ 155.01\times(\% \text{ Al}) \qquad (A1)$$

$$Tcr=895.12\times336.73\times(\% \text{ Si})/(\% \text{ Mn})-155.39\times(\% \\ \text{ Mn})+151.39\times(\% \text{ Al}) \qquad (B1)$$

TABLE 5

| | Internal oxidation starting temperature (° C.) | Si (mass %) | Mn (mass %) | Al (mass %) |
|---|---|---|---|---|
| Kind of steel A | 400 | 1.02 | 2.28 | 0.02 |
| Kind of steel B | 448 | 0.45 | 2.58 | 0.03 |
| Kind of steel C | 486 | 0.6 | 2.08 | 0.03 |
| Kind of steel D | 535 | 0.37 | 2.41 | 0.39 |

Then, the composition of the kind of steel A was substituted in the regression equation (B1). As a result, it was confirmed that the internal oxidation starting temperature Tcr was 395.6(° C.) and was substantially the same as the internal oxidation starting temperature Tcr determined by the second estimation method. In addition, when the internal oxidation starting temperature Tcr of the kind of steel A was estimated by another estimation method, it was possible to obtain an internal oxidation starting temperature Tcr of approximately 400° C.

Then, the cumulative temperature of any portion to be measured in the kind of steel A was calculated, using t0 as the coiling completion time and t1 as the time when the temperature T of the portion to be measured reached the internal oxidation starting temperature Tcr. The internal oxidation starting temperature Tcr was 395.6(° C.). Furthermore, the thicknesses of the internal oxide layers in these portions to be measured were actually measured. Then, simple regression analysis was performed on these values to calculate the proportional constant α. H0 was set to 0. The proportional constant α was set to $2\times10^{-5}$ μm/(° C.·min). The results are shown in FIG. 5.

Figure 5:
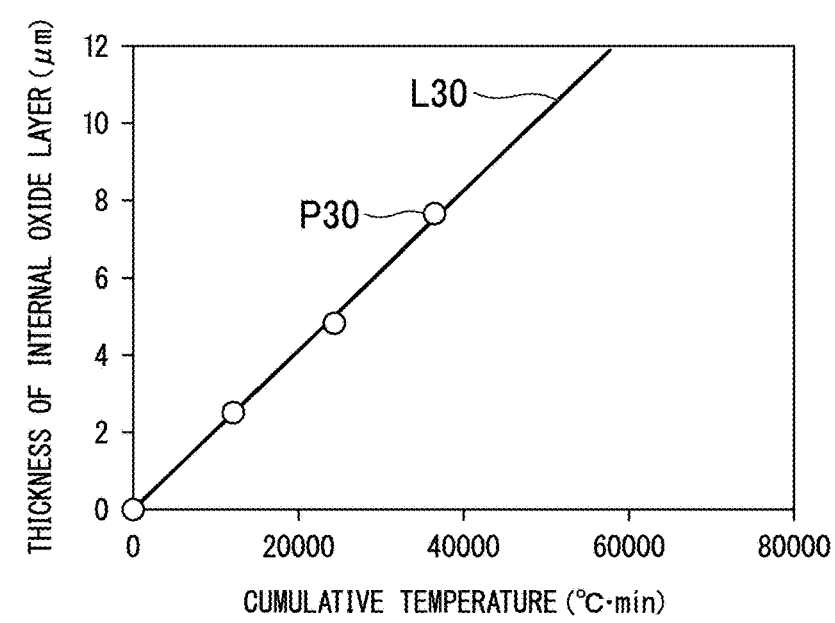
FIG. 5 is a graph showing an example of a correlation between the measured value of the thickness of the internal oxide layer and Expression (2) according to this embodiment.

In FIG. 5, P30 indicates the cumulative temperature and the measured value of the thickness of the internal oxide layer in each portion to be measured in the kind of steel A. A graph L30 shows Expression (2) calculated above, that is, the correlation between the cumulative temperature and the estimated value of the thickness of the internal oxide layer. As can be clearly seen from FIG. 5, Expression (2) has a very high correlation with the measured value of the thickness of the internal oxide layer. The degree-of-freedom determination coefficient $R^2$ in Expression (2) was 0.9989. In addition, substantially the same results were obtained even in a case in which the internal oxidation starting temperature Tcr was estimated using the regression equation (A1), but the degree-of-freedom determination coefficient of Expression (2) was slightly decreased. Further, the correlation expression is described here, using a cumulative temperature of 40,000° C.·min as a starting point. However, this is merely an example, and a method for determining the correlation expression is not limited to this example.

Therefore, since the internal oxidation starting temperature Tcr is determined on the basis of the composition of the hot-rolled steel sheet, it is possible to estimate the internal oxidation starting temperature. Tcr with high accuracy. Furthermore, the thickness of the internal oxide layer is estimated on the basis of the internal oxidation starting temperature Tcr estimated with high accuracy in this way and Expression (2) (that is, the cumulative temperature having a very high correlation with the thickness of the internal oxide layer). Therefore, it is possible to estimate the thickness of the internal oxide layer with high accuracy.

The preferred embodiment of the invention has been described in detail above. However, the invention is not limited to the embodiment. It is obvious that those skilled in the art to which the invention belongs can conceive of various changes or modification examples within the scope of the technical idea described in the claims. Of course, it is understood that these also fall within the technical scope of the invention.

BRIEF DESCRIPTION OF THE REFERENCE SYMBOLS

P1, P30: measurement point indicating cumulative temperature and measured value of thickness of internal oxide layer P3, P4: measurement point indicating internal oxidation starting temperature and correlation between measured value of thickness of internal oxide layer and cumulative temperature P10~P12: measurement point indicating coiling completion temperature and thickness of internal oxide layer L1, L30: graph indicating correlation between cumulative temperature and estimated value of thickness of internal oxide layer L10~L12: thickness-coiling temperature correlation graph

10: processing device

11: internal, oxidation starting temperature estimation unit

12: internal oxide layer thickness estimation unit

What is claimed is:

1. An internal oxidation starting temperature estimation device that estimates an internal oxidation starting temperature which is a minimum temperature required for an internal oxide layer to grow on a surface of an easily oxidizable element-containing hot-rolled steel sheet including Si, Mn, or Al or any combination thereof, the internal oxidation starting temperature estimation device comprising:

an internal oxidation starting temperature estimation unit that estimates the internal oxidation starting temperature on the basis of concentrations of the Si, the Mn, and the Al included in the easily oxidizable element-containing hot-rolled steel sheet, wherein the internal oxidation starting temperature estimation unit determines the internal oxidation starting temperature such that a correlation between a measured value of a thickness of the internal oxide layer and a cumulative temperature defined by the following Expression (1) is the highest, for each of a plurality of types of the easily oxidizable element-containing hot-rolled steel sheets in which the Si concentration, the Mn concentration, or the Al concentration or any combination thereof is different:

$$S_T = \int_{t0}^{t1} (T - Tcr)dt \qquad (1)$$

wherein, in Expression (1), $S_T$ is the cumulative temperature, T is a temperature of a portion to be estimated, in which the thickness of the internal oxide layer is to be estimated, in the easily oxidizable element-containing hot-rolled steel sheet, Tcr is the internal oxidation starting temperature, t0 is an estimation start time when estimation of the thickness of the internal oxide layer is started, t1 is an estimation evaluation time, and T−Tcr is 0 in an integration interval where T−Tcr is equal to or less than 0.

2. The internal oxidation starting temperature estimation device according to claim 1, wherein the internal oxide layer is formed when the easily oxidizable element-containing hot-rolled steel sheet is cooled in a coiled state.

3. The internal oxidation starting temperature estimation device according to claim 1, wherein the internal oxidation starting temperature estimation unit determines the internal oxidation starting temperature such that a sum of squared deviations when a quadratic function of the cumulative temperature is applied to the measured value of the thickness of the internal oxide layer is minimized, for each of the plurality of types of easily oxidizable element-containing hot-rolled steel sheets in which the Si concentration, the Mn concentration, or the Al concentration or any combination thereof is different.

4. An internal oxide layer thickness estimation device comprising:

an internal oxide layer thickness estimation unit that estimates the thickness of the internal oxide layer formed in the easily oxidizable element-containing hot-rolled steel sheet, on the basis of the internal oxidation starting temperature estimated by the internal oxidation starting temperature estimation device according to claim 1 and the following Expression (2):

$$H = \alpha \times S_T + H_0 \qquad (2)$$

in Expression (2), H is the thickness of the internal oxide layer, $S_T$ is the cumulative temperature, $\alpha$ is a proportional constant, and $H_0$ is an initial value of the thickness of the internal oxide layer.

5. An internal oxidation starting temperature estimation method that estimates an internal oxidation starting temperature which is a minimum temperature required for an internal oxide layer to grow on a surface of an easily oxidizable element-containing hot-rolled steel sheet including Si, Mn, or Al or any combination thereof, the internal oxidation starting temperature estimation method comprising:

an internal oxidation starting temperature estimation step of estimating the internal oxidation starting temperature with the internal oxidation starting temperature estimation device of claim 1, on the basis of concentrations of the Si, the Mn, and the Al included in the easily oxidizable element-containing hot-rolled steel sheet.

6. A program that causes a computer to estimate an internal oxidation starting temperature which is a minimum temperature required for an internal oxide layer to grow on a surface of an easily oxidizable element-containing hot-rolled steel sheet including Si, Mn, or Al or any combination thereof, the program causing the computer to execute:

an internal oxidation starting temperature estimation step of estimating the internal oxidation starting temperature on the basis of concentrations of the Si, the Mn, and the Al included in the easily oxidizable element-containing hot-rolled steel sheet, wherein the computer is the internal oxidation starting temperature estimation device according to claim 1.

* * * * *